United States Patent [19]

Saiki et al.

[11] Patent Number: 4,822,529

[45] Date of Patent: * Apr. 18, 1989

[54] ANTISTATIC AGENTS FOR SYNTHETIC FIBERS AND METHODS OF PRODUCING SAME

[75] Inventors: Masatsugu Saiki, Okazaki; Yoshio Imai; Makoto Takagi, both of Gamagori, all of Japan

[73] Assignee: Takemoto Yushi Kabushiki Kaisha, Aichi, Japan

[*] Notice: The portion of the term of this patent subsequent to Feb. 23, 2005 has been disclaimed.

[21] Appl. No.: 95,330

[22] Filed: Sep. 10, 1987

Related U.S. Application Data

[62] Division of Ser. No. 836,691, Mar. 6, 1986, Pat. No. 4,727,177.

[51] Int. Cl.$^4$ .............................................. C07F 9/09
[52] U.S. Cl. .................................................... 260/403
[58] Field of Search .......................................... 260/403

[56] References Cited

U.S. PATENT DOCUMENTS

| | | | |
|---|---|---|---|
| 3,539,601 | 11/1970 | Lewis | 260/403 |
| 3,775,446 | 11/1973 | Wegeroff et al. | 260/403 |
| 4,727,177 | 2/1988 | Saiki et al. | 558/87 |

FOREIGN PATENT DOCUMENTS 108767 5/1986 Japan.

*Primary Examiner*—Anton H. Sutto
*Attorney, Agent, or Firm*—Flehr, Hohbach, Test, Albritton & Herbert

[57] ABSTRACT

Antistatic agents for synthetic fibers comprising a specific type of quaternary ammonium alkyl phosphate as principal constituent and 1 weight percent or less of by-product alkali metal halides have improved antistatic characteristics both in high and low humidity conditions and reduce the amount of deposits that fall off, yellowing by a heat treatment and generation of rust. Methods of producing such antistatic agents are also disclosed.

2 Claims, No Drawings

ANTISTATIC AGENTS FOR SYNTHETIC FIBERS AND METHODS OF PRODUCING SAME

This is a division of application Ser. No. 836,691 filed Mar. 6, 1986, now U.S. Pat. No. 4,727,177.

This invention relates to antistatic agents for synthetic fibers and methods of producing such agents.

In general, static electricity presents problems to synthetic fibers not only in the manufacturing process of filament yarn and staple fiber, spinning process, weaving process and finishing process but also regarding products made from them. Static electricity impedes operations and lowers the quality of products by dislevelling and wrapping and producing fluff. It thus gives shocks to people, causes the clothes to stick and attracts dust particles. It therefore makes it necessary to use an antistatic agent with synthetic fibers but such an antistatic agent must be able to exhibit its effectiveness not only under a condition of high humidity but also when humidity is low.

During the production of synthetic fibers, finishing oils which fall off and become deposited on the machines during each process present serious problems. During a spinning process, for example, the fibers may be caused to wrap around a draft rubber roller. If they become deposited on a guide or a trumpet, these machine parts must be cleaned more frequently. If they become deposited on a heater during a spinning-drawing process, tar will be generated. If they become deposited on a guide during a warping process, they will generate fluff and cause yarn breakage. As the processing speed is increased, the problems caused by the deposit become even more serious and this necessarily implies that antistatic agents to be applied to synthetic fibers must have the property of not falling off at a significant rate. The present invention relates to antistatic agents for synthetic fibers having this required characteristic and methods of producing such agents.

There are many types of surface active agents (cationic, anionic, non-ionic and amphoteric) serving as antistatic agents for synthetic fibers. Alkyl phosphates exhibit favorable antistatic properties under conditions of high and medium humidity, do not fall off very much, do not turn yellow by a heat treatment and do not rust much, but are not as effective as should be as an antistatic agent in low humidity situations.

Quaternary ammonium salts such as trimethyl lauryl ammonium chloride, triethyl polyoxyethylene (3 mols) stearyl ammonium methosulfate, and tributyloctyl ammonium nitrate have also been used as antistatic agents. These quaternary ammonium salts are advantageous in that they exhibit favorable antistatic properties not only a high humidity but also at low humidity but they fall off, turn yellow by a heat treatment and generate rusts.

These problems associated with quaternary ammonium salts, however, are thought to be caused by the counter anions of quaternary ammonium cations. In fact, if the counter anion is $Cl^-$, rusting becomes a serious problem and if it is $NO_3^-$ or $CH_3SO_4^-$, yellowing becomes serious. Earlier, quaternary ammonium salts with phosphate anion introduced as counter anion came to be considered (Japanese Patent Tokko No. 45-573 and Tokkai No. 54-70223). These quaternary ammonium lower alkyl phosphates exhibit favorable antistatic properties both at high humidity and at low humidity and have the advantages of not turning yellow much by a heat treatment and not producing much rust, but have the problem of falling off significantly.

It is therefore an object of the present invention to eliminate the aforementioned problems by providing antistatic agents for synthetic fibers which are capable of exhibiting favorable antistatic properties under both high and low humidity conditions and do not fall off, turn yellow by a heat treatment or rust much.

It is a further object of the present invention to provide methods of producing antistatic agents for synthetic fibers having the aforementioned properties.

An antistatic agent for synthetic fibers according to this invention comprises quaternary ammonium alkyl phosphates shown by the formula (I) or (II) below as its principal constituent and no more than 1 wt% of by-product alkali metal halides with respect to the aforementioned quaternary ammonium alkyl phosphates:

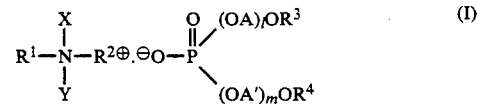

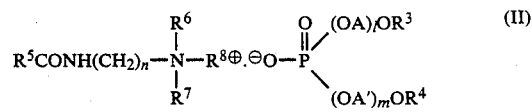

where $R^1$ and $R^3$ are alkyl group or alkenyl group with 8-18 carbon atoms, $R^2$, $R^6$, $R^7$ and $R^8$ are alkyl group with 1-3 carbon atoms, $R^4$ is hydrogen or alkyl or alkenyl group with 8-18 carbon atoms, $R^5$ is alkyl or alkenyl group with 7-17 carbon atoms, X is alkyl group with 1-3 carbon atoms or a group shown by $—(AO)_qH$, Y is alkyl group with 1-3 carbon atoms or a group shown by $—(A'O)_rH$, AO and A'O being the same respectively as OA and OA' in the formulas (I) and (II), q and r are integers in the range of 2-40 such that $q+r=4-42$, OA and OA' are a single oxyethylene or oxypropylene group or a block or random connected mixture thereof, l and m are each zero or an integer in the range of 1-20 such that $l+m=0-20$, and n is 2 or 3.

In the formulas (I) and (II), if the number of carbon atoms in $R^1$ and $R^3$ is less than 8 or that in $R^5$ is less than 7, the amount of deposit increases. If the content of by-product alkali metal halides exceeds 1 wt% with respect to the quaternary ammonium alkyl phosphate, there is increased yellowing by a heat treatment and rusting. For this reason and in particular for preventing rust, it is particularly preferable that the content of alkali metal halides be 0.3 wt% or less with respect to quaternary ammonium alkyl phosphate.

Examples of quaternary ammonium alkyl phosphate of the present invention shown by the formula (I) or (II) include combinations of the following quaternary ammonium cations and phosphate anions. The quaternary ammonium cation may be trimethyloctyl ammonium cation, triethylstearyl ammonium cation,

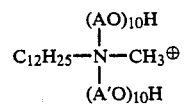

where AO and A'O are as in (I), triethyl octanoic amidopropyl ammonium cation, etc. The phosphate anion may be polyoxyethylene (3 mols) lauryl phosphate anion, polyoxyethylene (10 mols) stearyl phosphate anion, octyl phosphate anion, etc.

Because of their characteristic chemical structures, the quaternary ammonium alkyl phosphates of the present invention cannot be produced advantageously from a practical point of view by any of the conventional methods. There has been known a method, for example, of preventing alkali metal halides from being produced as by-products by direct reaction between tertiary amine and lower alkyl triester of phosphoric acid (Japanese patent Tokko No. 45-573 and Tokkai No. 54-70223), but since triesters of phosphoric acid with a long-chain alkyl group have low reactivity with tertiary amines, they are not practical for the production of quaternary ammonium long-chain alkyl phosphates.

According to another conventional method, an alkali metal salt of mono- and/or di-long-chain alkyl phosphate is reacted with mono-long-chain alkyl tri-short-chain alkyl ammonium halide by a salt exchange in water or an alcohol solvent such as methanol, isopropanol, etc. Quaternary ammonium alkyl phosphates are then produced by filtering inorganic by-product compounds such as alkali metal halides. Although this conventional method is popular for the production and refining of so-called complex salts which are combinations of anion and cation active agents, it is not appropriate for keeping the content of inorganic by-products to 1 wt% or less because both the quaternary ammonium halide and the alkali metal salt of alkyl phosphate to be used contain long-chain alkyl grups and it is stoichiometrically difficult to carry out the salt exchange reaction for increasing their concentrations to relatively high levels in the range of 10–50 wt% in water or alcohol-type solvent which are required for industrial reasons. Accordingly, there will remain unused quaternary ammonium halides and alkali metal salts of alkyl phosphate and this makes it practically impossible to reduce the content of alkali metal halides to 1 wt% or less with respect to quaternary ammonium alkyl phosphates.

Quaternary ammonium alkyl phosphates according to this invention can be produced by the method described below. First, tertiary amine shown by the following formula (1) or (2) is quaternalized by alkyl halide (with alkyl group given by $R^2$ or $R^8$ of (I) or (II)). Next, lower alcoholate of alkyl metal is used in the presence or absence of lower alcohol as solvent to exchange the halogen anions of the anion part with lower alcoxy anions, and after the alkali metal halides generated at this time as by-products are separated, mono- or di-alkyl phosphate shown by the following formula (3) is used to exchange the alcoxy anions:

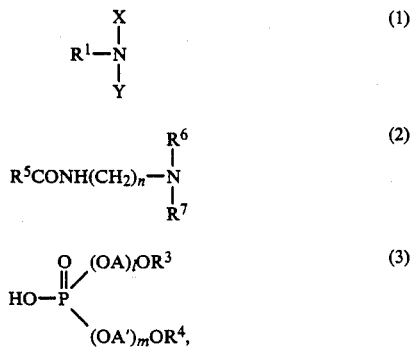

where $R^1$, $R^3$, $R^4$, $R^5$, $R^6$, $R^7$ X, Y, l, m and n are as defined above.

Examples of alkali metal alcoholate which may be used here include sodium methylate, sodium ethylate and potassium isopropoxide, but sodium methylate is industrially advantageous. Favorable results are obtained in view of the salt exchange reaction and the separation process thereafter, if lower alcohol such as methanol, ethanol and isopropanol is used as solvent. Thus, quarternary ammonium alkyl phosphates of the present invention are mixtures of mono alkyl phosphate and dialkyl phosphate of quarternary ammonium.

Quaternary ammonium alkyl phosphates of the present invention can be used singly as an antistatic component of a finishing oil for synthetic fibers but it is equally well to use them as a mixture with a conventional type of antistatic agent in an appropriate ratio.

The antistatic agents of this invention can be applied singly to synthetic fibers such as polyesters, polyacrylonitriles and polyamides or to their mixtures with natural and chemical fibers. The rate of applicaion to such synthetic fibers (inclusive of mixed fibers) is generally 0.01–2 wt% and preferably 0.01–0.5 wt%. They may be applied to filaments, a tow or staple fibers by a kiss-roll method, by dipping or by spraying either during or after a spinning process. They may also be applied to fiber products.

In what follows, the present invention and its effects will be explained further in detail by way of examples and comparisons and it should be understood that these examples are not intended to limit the scope of this invention.

SYNTHESIS OF QUATERNARY AMMONIUM ALKYL PHOSPHATE OF THIS INVENTION (EXAMPLE NO. 1)

One mol of phosphoric anhydride was added to three mols of octyl alcohol over a period of one hour at 60°–70° C. while stirring. They were allowed to react with each other at 70° C. for three hours and a mixture of mono and dioctyl phosphate was obtained. Separately, 0.5 mol of octyl dimethylamine and 200 ml of methanol were set inside an autoclave and after the interior gas was replaced by nitrogen, 0.5 molar equivalent of methyl chloride was introduced for a reaction at 60°–70° C. for three hours to obtain octyltrimethyl ammonium chloride. To this was gradually added 96 g of 28% sodium methylate-methanol solution (0.5 molar equivalent as sodium methylate) for salt exchange and the by-product sodium chloride was filtered away to obtain as filtrate a methanol solution of octyltrimethyl ammonium methoxide. To this methanol solution was added 0.5 mol of the aforementioned mixture of mono and dioctyl phosphate and after methanol was distilled away, it was diluted with water to obtain 50 wt% aqueous solution of octyltrimethyl ammonium octyl phosphate (Example No. 1).

SYNTHESIS OF QUATERNARY AMMONIUM ALKYL PHOSPHATE OF THIS INVENTION (EXAMPLE NO. 5)

One mol of octyl alcohol and 0.2 weight part of potassium hydroxide as catalyst with respect to 100 weight part of octyl alcohol were set inside an autoclave and after the interior gas was replaced by nitrogen, 4 mols of ethylene oxide was introduced at 120°–150° C. over a period of two hours for a reaction at 150° C. for one hour to obtain polyoxyethylene (4 mols) octylether. Next, 1 mol of phosphoric anhydride was added to 3 mols of this polyoxyethylene (4 mols) octylether thus obtained at 60°-70° C. over a period of one hour with stirring and they were allowed to react at 70° C. for three additional hours to obtain a mixture of polyoxyethylene (4 mols) mono- and di-octyl phosphates. Separately, 1.1 mol of diethyl aminopropylamide and 1 mol of capric acid were set inside an autoclave for reaction at 120°-150° C. for eight hours while nitrogen gas was introduced and generated water and distilled out of the system at normal pressure to obtain diethyl aminopropylamide. Next, 1 mol of diethyl aminopropylamide thus obtained and 200 ml of isopropyl alcohol were set inside an autoclave for a reaction at 80°-100° C. for three hours after the interior gas was replaced by nitrogen gas and 1 molar equivalent of ethyl chloride was introduced to obtain triethyloctylamide propyl ammonium chloride. To this was gradually added 193 g of 28% sodium methylate-methanol solution (1 molar equivalent as sodium methylate) for salt exchange and the by-product sodium chloride was filtered away to obtain as filtrate an isopropyl alcohol/methanol solution of triethyloctylamidepropyl ammonium methoxide. One mol of the aforementioned mixture of polyoxyethylene (4 moles) mono- and di-octyl phosphates was added to this isopropyl alcohol/methanol solution and after isopropyl alcohol/methanol was distilled away, it was diluted with water to obtain 50 wt% water solution of triethyloctylamidepropyl ammonium-polyoxyethylene (4 mols) octyl phosphate (Example No. 5).

SYNTHESIS OF QUATERNARY AMMONIUM ALKYL PHOSPHATE OF THIS INVENTION (EXAMPLE NO. 10)

One mol of phosphoric anhydride was added to 3 mols of stearyl alcohol at 70°-80° C. over a period of one hour with stirring and they were allowed to react at 80° C. for three additional hours to obtain a mixture of mono- and di-stearyl phosphates. Separately, 1 mol of stearyl amine and 0.5 weight part of potassium hydroxide as catalyst with respect to 100 weight part of stearyl amine were set inside an autoclave and after the interior gas was replaced by nitrogen, 30 mols of ethylene oxide was introduced at 100°-160° C. over a period of six hours for a reaction at 160° C. for one hour to obtain polyoxyethylene (30 mols) stearyl amino-ether. To this was added next 530 ml of isopropyl alcohol and after the interior gas was replaced by nitrogen again, 1 molar equivalent of methyl chloride was introduced for a reaction at 80-100 for three hours to obtain the compound A shown as follows:

   (A)

To this was gradually added 193 g of 28% sodium methylate-methanol solution (1 molar equivalent as sodium methylate) for salt exchange and the by-product sodium chloride was filtered away to obtain as filtrate an isopropyl alcohol/methanol solution of the compound B shown below:

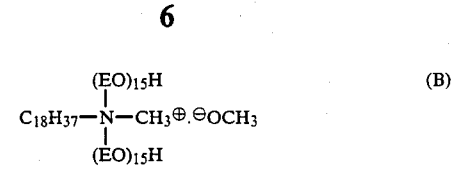   (B)

One mol of the aforementioned mixture of mono- and di-stearyl phosphates was added to this isopropyl alcohol/methanol solution and after isopropyl alcohol/methanol was distilled away, it was diluted with water to obtain 50 wt% water solution of Example No. 10.

Other quaternary ammonium alkyl phosphates (exclusive of Comparison Example No. 12) were synthesized as follows.

SYNTHESES OF EXAMPLES NOS. 2-4, 6-9 AND 10

Methods similar to those for Examples Nos. 1, 5 and 10 were respectively used.

SYNTHESES OF COMPARISON EXAMPLES NOS. 1-8

Methods similar to those for Examples Nos. 1, 5 and 10 were used.

COMPARISON EXAMPLES 9-12

Conventionally available products were used.

SYNTHESIS OF COMPARISON EXAMPLE NO. 13

This was done by heating to dissolve 347.5 g (1 mol) of stearyl trimethyl ammonium chloride and 334.7 g (1 mol) of sodium sesqui stearyl phosphate in 2000 ml of a mixed solvent of isopropyl alcohol/water=95/5 (volume ratio). The solution was heated and stirred for one hour at 60° C. and the deposited sodium chloride was filtered away by heating at 45°-50° C. Isopropyl alcohol was distilled from the filtered solution thus obtained while heating under a reduced pressure and trimethyl stearyl ammonium stearyl phosphate with 80% of solid component was obtained.

SYNTHESIS OF COMPARISON EXAMPLE NO. 14

This was done by heating to dissolve 347.5 g (1 mol) of stearyl trimethyl ammonium chloride and 668 g (1 molar equivalent) of 50% aqueous sodium sesqui stearyl phosphate in 2000 ml of isopropyl alcohol and 1000 ml of water and isopropyl alcohol was distilled away under azeotropy while the mixture was heated and stirred. Next, 1000 ml of isopropyl alcohol was added to dilute the solution and sodium chloride which deposited at 35°-40° C. was filtered away. Isopropyl alcohol was distilled away by heating under a reduced pressure from the filtered solution which had been obtained and trimethyl stearyl ammonium stearyl phosphate with 80% of solid component was obtained.

SYNTHESIS OF COMPARISON EXAMPLE NO. 15

This was obtained by a method similar to that for Comparison Example No. 13.

SYNTHESIS OF COMPARISON EXAMPLE NO. 16

This was obtained by a method similar to that for Comparison Example No. 14.

Each of Examples and Comparison Examples shown below (except Comparison Example No. 12) is described as follows: (1) cation part (2) anion part (mixture of mono and di as in the case of aforementioned Example No. 1, except Comparison Examples Nos. 9–12), and (3) content of alkali metal halide (NaCl or KCl) with respect to effective components (weight percent, measured by the Volhard method except for Comparison Examples Nos. 9–12). POE, POP and EO respectively stand for polyoxyethylene, polyoxypropylene and oxyethylene.

Example No. 1: (1) trimethyl octyl ammonium, (2) octyl phosphate, (3) 0.18.

Example No. 2: (1) trimethyl octyl ammonium, (2) stearyl phosphate, (3) 0.14.

Example No. 3: (1) trimethylstearyl ammonium, (2) octyl phosphate, (3) 0.14.

Example No. 4: (1) trimethylstearyl ammonium, (2) stearyl phosphate, (3) 0.10.

Example No. 5: (1) triethyl octanoic amido propyl ammonium, (2) POE (4 mols) octyl phosphate, (3) 0.20.

Example No. 6: (1) triethyl octanoic amido propyl ammonium, (2) POE (15 mols) stearyl phosphate, (3) 0.24.

Example No. 7: (1) triethyl stearoic amido propyl ammonium, (2) POE (2 mols)/POP (1 mol) octyl phosphate, (3) 0.23.

Example No. 8: (1) triethyl stearoic amido propyl ammonium, (2) POE (5 mols)/POP (1 mol) stearyl phosphate, (3) 0.24.

Example No. 9: (1)

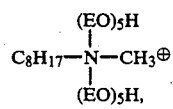

(2) octyl phosphate, (3) 0.63.

Example No. 10: (1)

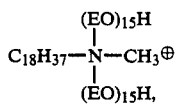

(2) stearyl phosphate, (3) 0.27.

Example No. 11: (1) trimethyloctyl ammonium, (2) octyl phosphate, (3) 0.80.

Comparison Example No. 1: (1) trimethylhexyl ammonium, (2) octyl phosphate, (3) 0.25.

Comparison Example No. 2: (1) trimethylhexyl ammonium, (2) stearyl phosphate, (3) 0.20.

Comparison Example No. 3: (1) trimethyloctyl ammonium, (2) butyl phosphate, (3) 0.34.

Comparison Example No. 4: (1) triethyl butanoic amido propyl ammonium, (2) octyl phosphate, (3) 0.75.

Comparison Example No. 5: (1) triethylbutanoic amido propyl ammonium, (2) stearyl phosphate, (3) 0.63.

Comparison Example No. 6: (1) monomethyl dioctylbutanoic amido propyl ammonium, (2) butyl phosphate, (3) 0.01.

Comparison Example No. B-7: (1)

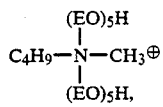

(2) octyl phosphate, (3) 0.83.

Comparison Example No. 8: (1)

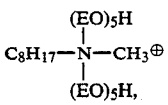

(2) butyl phosphate, (3) 0.72.

Comparison Example No. 9: (1) trimethyloctyl ammonium, (2) chloride.

Comparison Example No. 10: (1) triethyloctylamidpropyl ammonium, (2) methosulfate.

Comparison Example No. 11: (1)

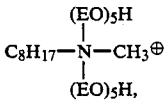

(2) nitrate.

Comparison Example No. 12: (1) potassium lauryl phosphate.

Comparison Example No. 13: (1) trimethylstearyl ammonium, (2) stearyl phosphate, (3) 2.10.

Comparison Example No. 14: (1) trimethylstearyl ammonium, (2) stearyl phosphate, (3) 1.43.

Comparison Example No. 15: (1) trimethyloctyl ammonium, (2) octyl phosphate, (3) 2.47.

Comparison Example No. 16: (1) trimethyloctyl ammonium, (2) octyl phosphate, (3) 1.71.

MEASUREMENT OF ELECTRICAL RESISTANCE AND EVALUATION OF YELLOWING

Staple fiber samples were prepared by applying 0.1% (effective weight percent) of each example and comparison example by a spray method to polyester staple fibers (1.4-denier, 38 mm) and dried for one hour at 60° C. These samples were left for 24 hours under the conditions of 25° C. and 40%RH or 25° C. and 65%RH, and their electrical resistance was measured. They were also subjected to a heat treatment at 150° C. for two hours and the degrees of their yellowing were observed and evaluated visually.

MEASUREMENT OF ELECTROSTATIC CHARGE GENERATED BY FRICTION

Pieces of refined woven acrylic cloth were immersed in 0.2% (effective weight percent) water solution of each example and comparison example and then dried for one hour at 60° C. They were left for 24 hours under the conditions of 25° C. and 40%RH and their static charges were measured by a rotary static tester.

EVALUATION OF DEPOSIT THAT FALL OFF

Staple filber samples were prepared by applying 0.12% (effective weight percent) of each example and comparison example by a spray method to polyester staple fibers (1.4-denier, 38 mm) and were left for 24 hours under the conditions of 30° C. and 70%RH.

These samples were used and 10 kg of slivers manufactured by a carding engine was passed through a drawing frame. The deposits that fall off and become adhered to the trumpet to which the sliver is taken up were visually observed. Grades A through E were assigned in the increasing order of the amount of deposits, grade A being given if this amount is very small.

EVALUATION OF RUSTING

After washed knitting needles were immersed in 2% (effective weight percent) water solutions of individual examples and comparison examples, they were left for 24 hours under the conditions of 20° C. and 100%RH and the appearance of rust on each needle was visually observed and evaluated.

The results of the above are shown in Tables 1 and 2.

TABLE 1

| Ex. No. | Resistance (Ω) 25° C., 40% RH | Resistance (Ω) 25° C., 65% RH | Static Charge (V) | Deposit | Yellowing | Rust |
|---|---|---|---|---|---|---|
| 1 | $1.2 \times 10^7$ | $8.8 \times 10^5$ | 100 | A | None | None |
| 2 | 4.3 | 16 | 200 | A | None | None |
| 3 | 5.7 | 33 | 170 | A | None | None |
| 4 | 8.5 | 53 | 450 | A | None | None |
| 5 | 3.2 | 13 | 180 | A | None | None |
| 6 | 6.5 | 45 | 250 | A | None | None |
| 7 | 6.3 | 43 | 210 | A | None | None |
| 8 | 8.8 | 74 | 470 | A | None | None |
| 9 | 1.3 | 9.0 | 100 | A | None | Slight |
| 10 | 3.3 | 21 | 120 | A | None | None |
| 11 | 1.5 | 8.5 | 100 | A | None | Slight |

TABLE 2

| Comp. Ex. No. | Resistance (Ω) 25° C., 40% RH | Resistance (Ω) 25° C. 65% RH | Static Charge (V) | Deposit | Yellowing | Rust |
|---|---|---|---|---|---|---|
| 1 | $1.0 \times 10^7$ | $11 \times 10^5$ | 110 | E | Slight | None |
| 2 | 4.2 | 10 | 170 | D | None | None |
| 3 | 3.2 | 9.5 | 100 | E | Slight | None |
| 4 | 3.5 | 21 | 210 | E | None | None |
| 5 | 4.7 | 3.5 | 350 | D | None | None |
| 6 | 15 | 170 | 700 | D | None | None |
| 7 | 1.3 | 12 | 100 | E | None | None |
| 8 | 1.1 | 8.8 | 100 | E | None | None |
| 9 | 3.5 | 22 | 210 | D | Present | Great |
| 10 | 3.1 | 36 | 480 | E | Present | Great |
| 11 | 7.7 | 44 | 400 | E | Present | Great |
| 12 | 600 | 890 | 1400 | A | None | None |
| 13 | 8.3 | 61 | 430 | B | Present | Great |
| 14 | 8.4 | 59 | 400 | A | Slight | Great |
| 15 | 1.1 | 17 | 90 | E | Slight | Great |
| 16 | 4.0 | 15 | 360 | D | Slight | Great |

A comparison between Tables 1 and 2 clearly demonstrate that the finishing oils of the present invention described hereinabove exhibit superior antistatic characteristics both in high humidity and low humidity conditions and reduce the amount of deposits that fall off, yellowing by a heat treatment and generation of rust.

What is claimed is:

1. In an antistatic agent for synthetic fibers comprising quaternary ammonium alkyl phosphate which is shown by the formula (I) below as principal constituent and by-product alkali metal halides;

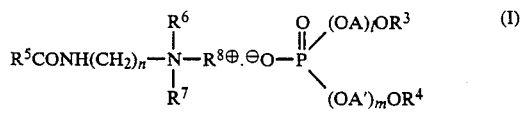

where $R^3$ is alkyl group or alkenyl group with 8-18 carbon atoms, $R^6$, $R^7$ and $R^8$ are each alkyl group with 1-3 carbon atoms, $R^4$ is hydrogen or alkyl group or alkenyl group with 8-18 carbon atoms, $R^5$ is alkyl group or alkenyl group with 7-17 carbon atoms, OA and OA' are single oxyethylene or oxypropylene group or block or random connected mixture thereof, l and m are 0 or integers in the range of 1-20 such that $l+m=0-20$, and n is 2 or 3, the improvement wherein said by-product alkali metal halides are contained by 1 weight percent or less with respect to said quaternary ammonium alkali phosphate.

2. A method of producing an antistatic agent for synthetic fibers comprising the steps of quaternalizing tertiary amine shown by the formula (1) by using alkyl halide with 1-3 carbon atoms, subsequently using alkali metal alcoholate to exchange halogen anions in anion section for alcoxy anions, separating alkali metal halide generated as a by-product, and subsequently exchanging said alcoxy anions by using mono- or di-alkyl phosphate shown by the formula (2) to thereby obtain quaternary ammonium alkyl phosphate which is shown by the formula (I) and contains 1 wt% or less of said by-product alkali metal halide, said quaternary ammonium alkyl phosphate serving as principal constituent of an antistatic agent for synthetic fibers:

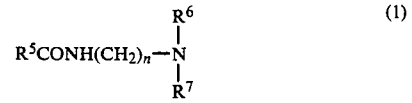

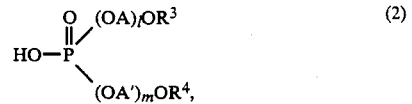

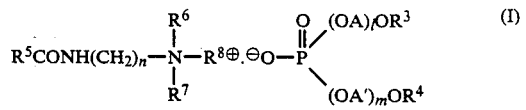

where $R^3$ is alkyl group or alkenyl group with 8-18 carbon atoms, $R^6$, $R^7$ and $R^8$ are each alkyl group with 1-3 carbon atoms, $R^4$ is hydrogen or alkyl group or alkenyl group with 8-18 carbon atoms, $R^5$ is alkyl group or alkenyl group with 7-17 carbon atoms, OA and OA' are single oxyethylene or oxypropylene group or block or random connected mixture thereof, l and m are 0 or integers in the range of 1-20 such that $l+m=0-20$, and n is 2 or 3.

* * * * *